(12) United States Patent
Gross et al.

(10) Patent No.: US 8,399,411 B2
(45) Date of Patent: Mar. 19, 2013

(54) COMPOSITION FOR ANIMAL CONSUMPTION AND METHOD FOR REDUCING MAP KINASE ACTIVITY

(75) Inventors: Kathy L. Gross, Topeka, KS (US); Inke Paetau-Robinson, Auburn, KS (US); Korinn E. Saker, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 82 days.

(21) Appl. No.: 12/781,360

(22) Filed: May 17, 2010

(65) Prior Publication Data

US 2010/0222279 A1    Sep. 2, 2010

Related U.S. Application Data

(62) Division of application No. 10/997,384, filed on Nov. 24, 2004, now Pat. No. 7,744,917.

(60) Provisional application No. 60/524,981, filed on Nov. 25, 2003.

(51) Int. Cl.
*A61K 38/00* (2006.01)

(52) U.S. Cl. .............................. 514/12; 426/2

(58) Field of Classification Search ........................ None
See application file for complete search history.

(56) References Cited

U.S. PATENT DOCUMENTS

| | | |
|---|---|---|
| 3,202,514 A | 8/1965 | Burgess et al. |
| 4,997,671 A | 3/1991 | Spanier |
| 4,997,672 A | 3/1991 | DeSimone et al. |
| 5,004,624 A | 4/1991 | Koschak et al. |
| 5,114,704 A | 5/1992 | Spanier et al. |
| 5,339,771 A | 8/1994 | Axelrod |
| 5,419,283 A | 5/1995 | Leo |
| 5,532,010 A | 7/1996 | Spanier et al. |
| 5,776,913 A | 7/1998 | Ogilvie et al. |
| 5,905,089 A | 5/1999 | Hwang et al. |
| 5,945,418 A | 8/1999 | Bemis et al. |
| 6,015,798 A | 1/2000 | Ogilvie et al. |
| 6,039,952 A | 3/2000 | Sunvold |
| 6,074,862 A | 6/2000 | Stein et al. |
| 6,203,825 B1 | 3/2001 | Hodgkins |
| 6,235,524 B1 | 5/2001 | Steller et al. |
| 6,316,464 B1 | 11/2001 | Cheng et al. |

(Continued)

FOREIGN PATENT DOCUMENTS

| | | |
|---|---|---|
| EP | 0678247 | 10/1995 |
| JP | 2002-519320 | 7/2002 |

(Continued)

OTHER PUBLICATIONS

Madani, S., et al., "Diacylglycerols Containing Omega 3 and Omega 6 Fatty Acids Bind to RasGRP and Modulate MAP Kinase Activation," J. Biol. Chem. 279 (2): 1176-1183 (Jan. 9, 2004).*

(Continued)

*Primary Examiner* — David J Blanchard
*Assistant Examiner* — Daniel F Coughlin
(74) *Attorney, Agent, or Firm* — Shannon McGarrah

(57) ABSTRACT

This invention is directed generally to compositions (including foods nutritional supplements, treats, and toys) for animal consumption, particularly compositions that comprise omega-3 and omega-6 polyunsaturated fatty acids, and particularly compositions that tend to aid in reducing mitogen-activated-protein ("MAP") kinase activity in animals. This invention also is directed generally to methods for using such compositions, particularly to methods for using such compositions to reduce MAP kinase activity in animals, and particularly to methods for using such compositions to treat a cancer or tissue hyperplasia. This invention is further directed generally to processes for making such compositions.

6 Claims, 3 Drawing Sheets

U.S. PATENT DOCUMENTS

| | | |
|---|---|---|
| 6,379,727 B1 | 4/2002 | Addy |
| 6,410,063 B1 | 6/2002 | Jewell et al. |
| 7,084,175 B2 * | 8/2006 | Wilson et al. ............... 514/558 |
| 2003/0194478 A1 | 10/2003 | Davenport et al. |

FOREIGN PATENT DOCUMENTS

| | | |
|---|---|---|
| WO | WO 97/13415 | 4/1997 |
| WO | WO 99/53927 | 10/1999 |
| WO | WO 00/26634 | 5/2000 |
| WO | WO 01/37678 | 5/2001 |
| WO | WO 01/58448 | 8/2001 |
| WO | WO 02/15719 | 2/2002 |
| WO | WO 2005/051093 | 6/2005 |

OTHER PUBLICATIONS

Collett, E., et al., n-6 and n-3 polyunsaturated fatty acids differentially modulate oncogenic Ras activation in colonocytes, Am. J. Physiol. Cell Physiol. 280: C1066-C1075 (2001).*

Tognon, C, et al., "Regulation of RasGRP via a Phorbol Ester-Responsive C1 Domain," Molecular and Cell Biology 18(12): 6995-7008 (1998).*

International Search Report and Written Opinion for PCT/US2004/039852.

"Southern Rock Lobster", 1996, www.sea-ex.com/fishphotos/lobstersthn.htm.

AAFCO Official Publication, 2003, p. 220.

AAFCO Official Publication, 2003, pp. 126-140.

Cowing et al., 2001, "Polyunsaturated Fatty Acids and Epidermal Growth Factor Receptor/Mitogen-Activated Protein Kinase Signaling in Mammary Cancer", Journal of Nutrition 131:1125-1128.

Hand, 2000, Small Animal Clinical Nutrition, pp. 401,403,411,455-457, 887-898.

Ogilvie et al., 1999, "Canine Cancer", Hill's Pet Nutrition.

* cited by examiner

COMPOSITION FOR ANIMAL CONSUMPTION AND METHOD FOR REDUCING MAP KINASE ACTIVITY

PRIORITY CLAIM TO RELATED PATENT APPLICATION

This application is a divisional application of U.S. patent application Ser. No. 10/997,384 filed Nov. 24, 2004, now U.S. Pat. No. 7,744,917 issued on Jun. 29, 2010, which claims priority to U.S. Provisional Patent Application Ser. No. 60/524,981 (filed Nov. 25, 2003). The entire text of the above referenced patent applications are incorporated by reference into this patent.

FIELD OF THE INVENTION

This invention is directed generally to compositions (including foods nutritional supplements, treats, and toys) for animal consumption, particularly compositions that comprise omega-3 and omega-6 polyunsaturated fatty acids, and particularly compositions that tend to aid in reducing mitogen-activated-protein ("MAP") kinase activity in animals. This invention also is directed generally to methods for using such compositions, particularly to methods for using such compositions to reduce MAP kinase activity in animals, and particularly to methods for using such compositions to treat a cancer or tissue hyperplasia. This invention is further directed generally to processes for making such compositions.

BACKGROUND OF THE INVENTION

MAP kinase activation is believed to enhance cell proliferation and carcinogenesis. Increased MAP kinase activity has been observed in cancerous tissue vs. normal counterparts. There also is reported evidence that tumor MAP kinase activity level predicts survival time in breast cancer patients, specifically, lower MAPK activity in mammary tissue has been reported to correlate with longer survival time.

Reducing MAP kinase activation is believed to generally be beneficial for treating conditions that involve abnormalities of cell proliferation, cell growth, cell differentiation, cell migration, and cell invasion. Such conditions include, for example, cancer and tissue hyperplasias of the gastrointestinal tract, immune system, prostate, kidney, mammary glands, and heart. Numerous patent publications discuss modulation of MAP kinase. See, e.g., U.S. Pat. No. 5,905,089. See also, U.S. Pat. No. 5,945,418. See also, U.S. Pat. No. 6,074,862. See also, U.S. Pat. No. 6,235,524. See also, U.S. Pat. No. 6,316,464. See also, Int'l Patent Appl. Publ. No. WO 01/58448. See also, Int'l Patent Appl. Publ. No. WO 00/26634. See also, Int'l Patent Appl. Publ. No. WO 99/53927.

An animal formulation that reportedly treats cachexia is discussed in U.S. Pat. No. 6,015,798 ("the '798 patent"). See also, U.S. Pat. No. 5,776,913. Both patents discuss a formulation shown in Table 1 below.)

TABLE 1

| Component | % by weight on a dry matter basis |
| --- | --- |
| Carbohydrate | 15-27 |
| Protein | 35-48 |
| Fat | 27-35 |
| Omega-3 Fatty Acid | 2.5-7.5 |
| Omega-6 Fatty Acid | 2.0-6.0 |
| Arginine | 2.0-3.5 |
| Nutritional balancing agents such as vitamins (A, $B_1$, $B_2$, $B_6$, E) and minerals (Ca, P, Na, K, Mg, Fe, Cl) | 0.4-1.0 |

Despite the foregoing, there continues to be a need for compositions for animal consumption, particularly those that aid in reducing MAP kinase activity, and particularly those that aid in treating cancers and tissue hyperplasias.

SUMMARY OF THE INVENTION

This invention is directed to compositions, and particularly compositions for animal consumption that tend to aid in reducing MAP kinase activity in animals. This invention particularly contemplates compositions for consumption by domestic cats or domestic dogs. It is contemplated, however, that the compositions also are generally suitable for use with, for example, other mammals, including non-human mammals such as non-human primates (e.g., monkeys, chimpanzees, etc.), companion animals (e.g., horses, etc.), farm animals (e.g., goats, sheep, pigs, cattle, etc.), laboratory animals (e.g., mice, rats, etc.), and wild and zoo animals (e.g., wolves, bears, deer, etc.). It also is contemplated that such compositions are suitable for use with non-mammalian animals, such as companion, farm, zoo, and wild birds (e.g., including, for example, song birds, parrots, ducks, geese, chickens, turkeys, ostriches, etc.).

Briefly, therefore, this invention is directed, in part, to a composition. The composition generally has a protein content of at least about 35% by weight on a dry matter basis, a carbohydrate content of less than about 30% by weight on a dry matter basis, and omega-3 polyunsaturated fatty acids and omega-6 polyunsaturated fatty acids. The weight ratio of the omega-6 polyunsaturated fatty acids to the omega-3 polyunsaturated fatty acids is from about 0.3:1 to about 5:1. In some embodiments, the fat content is at least about 8% by weight on a dry matter basis. In other embodiments, the fat content is less than about 27% by weight on a dry matter basis.

This invention also is directed, in part, to therapeutic compositions comprising a composition described above. Such therapeutic compositions include compositions for reducing MAP kinase activity. Such therapeutic compositions also include compositions for treating a cancer. Such therapeutic compositions also include compositions for treating a tissue hyperplasia.

This invention also is directed, in part, to a nutritional supplement, wherein the supplement comprises omega-3 polyunsaturated fatty acids and omega-6 polyunsaturated fatty acids. The weight ratio of the omega-6 polyunsaturated fatty acids to the omega-3 polyunsaturated fatty acids is from about 0.3:1 to about 5:1.

This invention also is directed, in part, to a treat, wherein the treat comprises omega-3 polyunsaturated fatty acids and omega-6 polyunsaturated fatty acids. The weight ratio of the omega-6 polyunsaturated fatty acids to the omega-3 polyunsaturated fatty acids is from about 0.3:1 to about 5:1.

This invention also is directed, in part, to a toy, wherein the toy comprises omega-3 polyunsaturated fatty acids and omega-6 polyunsaturated fatty acids. The weight ratio of the omega-6 polyunsaturated fatty acids to the omega-3 polyunsaturated fatty acids is from about 0.3:1 to about 5:1.

This invention also is directed, in part, to processes for preparing the compositions, nutritional supplements, treats, and toys described above.

This invention also is directed, in part, to methods for using the compositions, nutritional supplements, treats, and toys described above to aid in reducing MAP kinase activity.

This invention also is directed, in part, to methods for using the compositions, nutritional supplements, treats, and toys described above to treat a cancer, particularly a cancer associated with or dependent on MAP kinase activity, or a cancer treatable by reducing, inhibiting, or delaying the onset of MAP kinase activity.

This invention also is directed, in part, to methods for using the compositions, nutritional supplements, treats, and toys described above to treat a tissue hyperplasia, particularly a hyperplasia associated with or dependent on MAP kinase activity, or a hyperplasia treatable by reducing, inhibiting, or delaying the onset of MAP kinase activity.

Further benefits of our invention will be apparent to one skilled in the art from reading this specification.

DETAILED DESCRIPTION OF PREFERRED EMBODIMENTS

Figure 1:
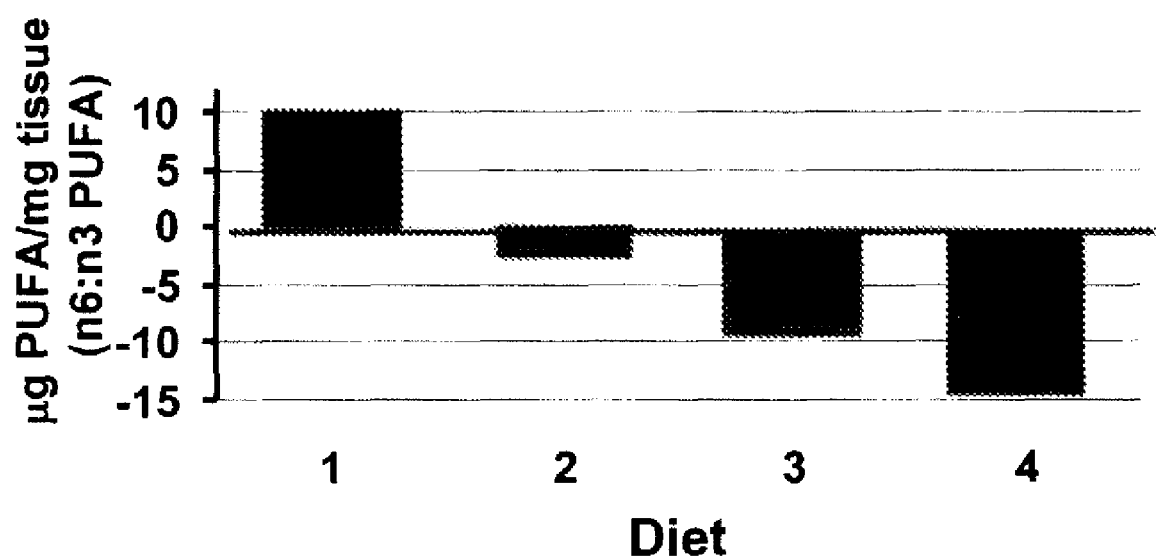
FIG. 1 illustrates the observed change in polyunsaturated fatty acid (PUFA) from baseline in adipose tissue as a function of the ratio of omega-6 to omega-3 (n6:n3) fatty acid in the diet. In this experiment, the tested diets had the following n6:n3 ratios: Diet 1: from about 4.5 to about 5; Diet 2: from about 2.3 to about 2.5; Diet 3: from about 1 to about 1.2; and Diet 4: from about 0.4 to about 0.5.

This detailed description of preferred embodiments is intended only to acquaint others skilled in the art with Applicants' invention, its principles, and its practical application so that others skilled in the art may adapt and apply the invention in its numerous forms, as they may be best suited to the requirements of a particular use. This detailed description and its specific examples, while indicating preferred embodiments of this invention, are intended for purposes of illustration only. This invention, therefore, is not limited to the preferred embodiments described in this specification, and may be variously modified.

As noted above, this invention is directed, in part, to compositions for animal consumption, and particularly compositions that tend to aid in reducing MAP kinase activity in animals. It is contemplated that the compositions of this invention may, for example, be used to treat cancers and tissue hyperplasias, particularly cancers and tissue hyperplasias associated with or dependent on MAP kinase activity, or cancers treatable by reducing, inhibiting, or delaying the onset of MAP kinase activity. Such treatment may include ameliorating, suppressing, eradicating, reducing the severity of decreasing the frequency of incidence of, preventing, reducing the risk of, and/or delaying the onset of cancer.

Without being bound by any particular theory, Applicants believe that the compositions of this invention may reduce MAP kinase activity by reducing one or more MAP kinase enzyme activation pathways. It is contemplated that such reduction of activity, however, may alternatively (or additionally) be the result of deactivation of activated MAP kinase itself.

The compositions of this invention generally have a protein content of at least about 35% by weight on a dry matter basis. In some embodiments, the protein content is at least about 48% by weight on a dry matter basis. In some embodiments, the protein content is at least about 49% by weight on a dry matter basis. In some embodiments, the protein content is from about 35% to about 75% by weight on a dry matter basis. In some embodiments, the protein content is from about 48% to about 75% by weight on a dry matter basis. In some embodiments, the protein content is from about 50% to about 75% by weight on a dry matter basis. In some embodiments, the protein content is from about 50% to about 70% by weight on a dry matter basis. In some embodiments, the protein content is from about 55% to about 65% by weight on a dry matter basis.

The compositions of this invention generally have a carbohydrate content of less than about 30% by weight on a dry matter basis. In some embodiments, the carbohydrate content is from about 3% to about 30% by weight on a dry matter basis. In some embodiments, the carbohydrate content is from about 3% to less than about 15% by weight on a dry matter basis. In some embodiments, the carbohydrate content is from about 5% to about 27% by weight on a dry matter basis. In some embodiments, the carbohydrate content is less than about 15% by weight on a dry matter basis. In some embodiments, the carbohydrate content is less than about 14% by weight on a dry matter basis. In some embodiments, the carbohydrate content is less than about 13% by weight on a dry matter basis. In some embodiments, the carbohydrate content is less than about 12% by weight on a dry matter basis. In some embodiments, the carbohydrate content is less than about 11% by weight on a dry matter basis. In some embodiments, the carbohydrate content is from about 6 to about 11% by weight on a dry matter basis.

In some embodiments, the fat content of the compositions of this invention is at least about 8% by weight on a dry matter basis. In some embodiments, the fat content is from about 8% to about 35% by weight on a dry matter basis. In some embodiments, the fat content is from about 8% to about 27% by weight on a dry matter basis. In some embodiments, the fat content is from about 8% to about 25% by weight on a dry matter basis. In some embodiments, the fat content is from about 10% to about 25% by weight on a dry matter basis. In some such embodiments, the fat content is from about 13% to about 20% by weight on a dry matter basis. In some embodiments, the fat content is from about 10% to about 35% by weight on a dry matter basis. In some embodiments, the fat content is from about 24% to about 35% by weight on a dry matter basis. In some embodiments, the fat content is from about 25% to about 35% by weight on a dry matter basis. In some embodiments, the fat content is from about 30% to about 35% by weight on a dry matter basis.

In other embodiments, the fat content of the compositions of this invention is less than about 27% by weight on a dry matter basis. In some embodiments, the fat content is less than about 25% by weight on a dry matter basis. In some embodiments, the fat content is from about 8% to about 20% by weight on a dry matter basis.

The compositions of this invention generally comprise omega-3 polyunsaturated fatty acids and omega-6 polyunsaturated fatty acids. In some embodiments, the omega-3 polyunsaturated fatty acid content is from about 2.5% to about 7.5% by weight on a dry matter basis. In some embodiments, the omega-3 polyunsaturated fatty acid content is from about 7.0% to about 7.5% by weight on a dry matter basis. In some embodiments, the omega-6 polyunsaturated fatty acid content is from about 2.0% to about 6.0% by weight on a dry matter basis. In some embodiments, the omega-6 polyunsaturated fatty acid content is from about 2.0% to about 2.5% by weight on a dry matter basis. The weight ratio of the omega-6 polyunsaturated fatty acids to the omega-3 polyunsaturated fatty acids is generally from about 0.3:1 to about 5:1. In some embodiments, the ratio is from about 0.4:1 to about 0.5:1. In some embodiments, the ratio is from about 1:1 to about 1.2:1. In some embodiments, the ratio is from about 2.3:1 to about 2.5:1. In some embodiments, the ratio is from about 4.5:1 to about 5:1.

It is contemplated that the compositions of this invention will include omega-3 polyunsaturated fatty acids comprising less than 20 carbon atoms, omega-3 polyunsaturated fatty acids comprising at least 20 carbon atoms, omega-6 polyunsaturated fatty acids comprising less than 20 carbon atoms, and omega-6 polyunsaturated fatty acids comprising at least 20 carbon atoms. Omega-3 and omega-6 polyunsaturated fatty acids having no greater than 20 carbon atoms preferably are $C_{18}$-$C_{20}$ polyunsaturated fatty acids, and omega-3 and omega-6 polyunsaturated fatty acids having at least 20 carbon atoms preferably are $C_{20}$-$C_{22}$ polyunsaturated fatty acids.

In some embodiments, the concentration of omega-3 polyunsaturated fatty acids with less than 20 carbon atoms is from about 0.9% to about 1.2% by weight of the composition on a dry matter basis. In some embodiments, the concentration of omega-3 polyunsaturated fatty acids with greater than 20 carbon atoms is from about 4.2% to about 6.0% by weight of the composition on a dry matter basis. In some embodiments, the concentration of omega-6 polyunsaturated fatty acids with less than 20 carbon atoms is from about 1.9% to about 4.8% by weight of the composition on a dry matter basis. In some embodiments, the concentration of omega-6 polyunsaturated fatty acids with greater than 20 carbon atoms is from about 1.0% to about 1.3% by weight of the composition on a dry matter basis.

In some embodiments, the concentration of omega-3 polyunsaturated fatty acids with less than 20 carbon atoms is from about 0.9% to about 1.2% by weight of the composition on a dry matter basis, and the concentration of omega-6 polyunsaturated fatty acids with less than 20 carbon atoms is from about 1.9% to about 4.8% by weight of the composition on a dry matter basis.

In some embodiments, the concentration of omega-3 polyunsaturated fatty acids with less than 20 carbon atoms is from about 0.9% to about 1.2% by weight of the composition on a dry matter basis, the concentration of omega-3 polyunsaturated fatty acids with greater than 20 carbon atoms is from about 4.2% to about 6.0% by weight of the composition on a dry matter basis, and the concentration of omega-6 polyunsaturated fatty acids with less than 20 carbon atoms is from about 1.9% to about 4.8% by weight of the composition on a dry matter basis.

In some embodiments, the concentration of omega-3 polyunsaturated fatty acids with less than 20 carbon atoms is from about 0.9% to about 1.2% by weight of the composition on a dry matter basis, the concentration of omega-3 polyunsaturated fatty acids with greater than 20 carbon atoms is from about 4.2% to about 6.0% by weight of the composition on a dry matter basis, the concentration of omega-6 polyunsaturated fatty acids with less than 20 carbon atoms is from about 1.9% to about 4.8% by weight of the composition on a dry matter basis, and the concentration of omega-6 polyunsaturated fatty acids with greater than 20 carbon atoms is from about 1.0% to about 1.3% by weight of the composition on a dry matter basis.

In some embodiments, the concentration of omega-3 polyunsaturated fatty acids with no greater than 20 carbon atoms is from about 0.9% to about 1.2% by weight of the composition on a dry matter basis. In some embodiments, the concentration of omega-3 polyunsaturated fatty acids with at least 20 carbon atoms is from about 4.2% to about 6.0% by weight of the composition on a dry matter basis. In some embodiments, the concentration of omega-6 polyunsaturated fatty acids with no greater than 20 carbon atoms is from about 1.9% to about 4.8% by weight of the composition on a dry matter basis. In some embodiments, the concentration of omega-6 polyunsaturated fatty acids with at least 20 carbon atoms is from about 1.0% to about 1.3% by weight of the composition on a dry matter basis.

In some embodiments, the composition comprises substantially no arginine. In some embodiments, for example, the composition comprises less than 2% arginine by weight on a dry matter basis. In other embodiments, for example, the composition comprises less than 1% arginine by weight on a dry matter basis. In other embodiments, for example, the composition comprises 0% (or essentially no) arginine by weight on a dry matter basis.

Some contemplated embodiments are directed to high-protein compositions. In some such contemplated embodiments, for example, the composition comprises a fat content of from about 8% to about 35% by weight on a dry matter basis; a protein content of at least about 48% by weight on a dry matter basis; a carbohydrate content of from about 3% to about 30% by weight on a dry matter basis; and omega-3 polyunsaturated fatty acids and omega-6 polyunsaturated fatty acids such that (a) the weight ratio of the omega-6 polyunsaturated fatty acids to the omega-3 polyunsaturated fatty acids is from about 0.3:1 to about 5:1, (b) the concentration of omega-3 polyunsaturated fatty acids in the composition is from about 2.5 to about 7.5% by weight on a dry matter basis, and (c) the concentration of omega-6 polyunsaturated fatty acids in the composition is from about 2.0 to about 6.0% by weight on a dry matter basis. In some such embodiments, the protein concentration is from about 50% to about 75% by weight of the composition on a dry matter basis. Particularly preferred embodiments of these high-protein compositions are illustrated in Tables 2-4 below (in each such embodiment, the weight ratio of omega-6 to omega-3 fatty acid being of from about 0.3:1 to about 5:1).

TABLE 2

| Component | Preferred proportion of the composition (% of dry weight of composition) |
|---|---|
| Carbohydrate | from about 3 to about 30 |
| Protein | from about 48 to about 75 |
| Fat | from about 8 to about 35 |
| Omega-3 Fatty Acids | from about 2.5 to about 7.5 |
| Omega-6 Fatty Acids | from about 2 to about 6 |

TABLE 3

| Component | Preferred proportion of the composition (% of dry weight of composition) |
|---|---|
| Carbohydrate | from about 5 to about 27 |
| Protein | from about 50 to about 75 |
| Fat | from about 10 to about 35 |
| Omega-3 Fatty Acids with <C20 | from about 0.9 to about 1.2 |
| Omega-3 Fatty Acids with <C20 | from about 4.2 to about 6.0 |
| Omega-6 Fatty Acids with >C20 | from about 1.9 to about 4.8 |
| Omega-6 Fatty Acids with >C20 | from about 1.0 to about 1.3 |
| Nutritional balancing agents, such as vitamins, minerals etc. | from about 0 to about 2 |

TABLE 4

| Component | Preferred proportion of the composition (% of dry weight of composition) |
|---|---|
| Carbohydrate | from about 6 to about 11 |
| Protein | from about 55 to about 65 |
| Fat | from about 25 to about 35 |
| Omega-3 Fatty Acids with <C20 | from about 0.9 to about 1.2 |
| Omega-3 Fatty Acids with <C20 | from about 4.2 to about 6.0 |
| Omega-6 Fatty Acids with >C20 | from about 1.9 to about 4.8 |
| Omega-6 Fatty Acids with >C20 | from about 1.0 to about 1.3 |
| Nutritional balancing agents, such as vitamins, minerals etc. | from about 0 to about 1.0 |

Some contemplated embodiments are directed to low-fat compositions. To illustrate, some such compositions comprise a fat content of from about 8% to about 27% by weight on a dry matter basis; a protein content of from about 35 to about 75% by weight on a dry matter basis; a carbohydrate content of from about 3% to about 30% by weight on a dry matter basis; and omega-3 polyunsaturated fatty acids and omega-6 polyunsaturated fatty acids such that (a) the weight ratio of the omega-6 polyunsaturated fatty acids to the omega-3 polyunsaturated fatty acids is from about 0.3:1 to about 5:1, (b) the concentration of omega-3 polyunsaturated fatty acids in the composition is from about 2.5 to about 7.5% by weight on a dry matter basis, and (c) the concentration of omega-6 polyunsaturated fatty acids in the composition is from about 2.0 to about 6.0% by weight on a dry matter basis. In some such embodiments, the fat content is from about 10% to about 25% by weight on a dry matter basis. Particularly preferred embodiments of these low-fat compositions are illustrated in Tables 5-7 below (in each such embodiment, the weight ratio of omega-6 to omega-3 fatty acid being of from about 0.3:1 to about 5:1).

TABLE 5

| Component | Preferred proportion of the composition (% of dry weight of composition) |
|---|---|
| Carbohydrate | from about 3 to about 30 |
| Protein | from about 35 to about 75 |
| Fat | from about 8 to about 27 |
| Omega-3 Fatty Acids | from about 2.5 to about 7.5 |
| Omega-6 Fatty Acids | from about 2 to about 6 |

TABLE 6

| Component | Preferred proportion of the composition (% of dry weight of composition) |
|---|---|
| Carbohydrate | from about 5 to about 27 |
| Protein | from about 50 to about 70 |
| Fat | from about 10 to about 25 |
| Omega-3 Fatty Acids with <C20 | from about 0.9 to about 1.2 |
| Omega-3 Fatty Acids with <C20 | from about 4.2 to about 6.0 |
| Omega-6 Fatty Acids with >C20 | from about 1.9 to about 4.8 |
| Omega-6 Fatty Acids with >C20 | from about 1.0 to about 1.3 |
| Nutritional balancing agents, such as vitamins, minerals etc. | from about 0 to about 2 |

TABLE 7

| Component | Preferred proportion of the composition (% of dry weight of composition) |
|---|---|
| Carbohydrate | from about 6 to about 11 |
| Protein | from about 55 to about 65 |
| Fat | from about 13 to about 20 |
| Omega-3 Fatty Acids with <C20 | from about 0.9 to about 1.2 |
| Omega-3 Fatty Acids with <C20 | from about 4.2 to about 6.0 |
| Omega-6 Fatty Acids with >C20 | from about 1.9 to about 4.8 |
| Omega-6 Fatty Acids with >C20 | from about 1.0 to about 1.3 |
| Nutritional balancing agents, such as vitamins, minerals etc. | from about 0 to about 1.0 |

Some contemplated embodiments are directed to low-carbohydrate compositions. To illustrate, some such compositions may comprise a fat content of at least about 8% by weight on a dry matter basis; a protein content of at least about 35% by weight on a dry matter basis; a carbohydrate content of less than about 15% by weight on a dry matter basis; and omega-3 polyunsaturated fatty acids and omega-6 polyunsaturated fatty acids such that (a) the weight ratio of the omega-6 polyunsaturated fatty acids to the omega-3 polyunsaturated fatty acids is from about 0.3:1 to about 5:1, (b) the concentration of omega-3 polyunsaturated fatty acids in the composition is from about 2.5 to about 7.5% by weight on a dry matter basis, and (c) the concentration of omega-6 polyunsaturated fatty acids in the composition is from about 2.0 to about 6.0% by weight on a dry matter basis. Particularly preferred embodiments of these low-carbohydrate compositions are illustrated in Tables 8-10 below (in each such embodiment, the weight ratio of omega-6 to omega-3 fatty acid being of from about 0.3:1 to about 5:1).

TABLE 8

| Component | Preferred proportion of the composition (% of dry weight of composition) |
|---|---|
| Carbohydrate | from about 3 to about less than 15 |
| Protein | from about 35 to about 75 |
| Fat | from about 8 to about 35 |
| Omega-3 Fatty Acids | from about 2.5 to about 7.5 |
| Omega-6 Fatty Acids | from about 2 to about 6 |

TABLE 9

| Component | Preferred proportion of the composition (% of dry weight of composition) |
|---|---|
| Carbohydrate | from about 6 to about 11 |
| Protein | from about 50 to about 70 |

TABLE 9-continued

| Component | Preferred proportion of the composition (% of dry weight of composition) |
|---|---|
| Fat | from about 24 to about 35 |
| Omega-3 Fatty Acids with <C20 | from about 0.9 to about 1.2 |
| Omega-3 Fatty Acids with >C20 | from about 4.2 to about 6.0 |
| Omega-6 Fatty Acids with <C20 | from about 1.9 to about 4.8 |
| Omega-6 Fatty Acids with >C20 | from about 1.0 to about 1.3 |
| Nutritional balancing agents, such as vitamins, minerals etc. | from about 0 to about 2 |

TABLE 10

| Component | Preferred proportion of the composition (% of dry weight of composition) |
|---|---|
| Carbohydrate | from about 6 to about 11 |
| Protein | from about 55 to about 65 |
| Fat | from about 30 to about 35 |
| Omega-3 Fatty Acids with <C20 | from about 0.9 to about 1.2 |
| Omega-3 Fatty Acids with >C20 | from about 4.2 to about 6.0 |
| Omega-6 Fatty Acids with <C20 | from about 1.9 to about 4.8 |
| Omega-6 Fatty Acids with >C20 | from about 1.0 to about 1.3 |
| Nutritional balancing agents, such as vitamins, minerals etc. | from about 0 to about 1.0 |

In some contemplated embodiments, the composition comprises a fat content of at least about 8% by weight on a dry matter basis, a protein content of at least about 35% by weight on a dry matter basis, a carbohydrate content of less than about 11% by weight on a dry matter basis, and omega-3 polyunsaturated fatty acids and omega-6 polyunsaturated fatty acids such that the weight ratio of the omega-6 polyunsaturated fatty acids to the omega-3 polyunsaturated fatty acids is from about 0.3:1 to about 5:1. In some such contemplated embodiments, the fat content is from about 30% to about 35% by weight on a dry matter basis. In other such contemplated embodiments, the fat content is from about 13% to about 20% by weight on a dry matter basis. In other such contemplated embodiments, the protein content is from about 50% to about 70% by weight on a dry matter basis. In other such contemplated embodiments, the fat content is from about 13% to about 20% by weight on a dry matter basis; and the protein content is from about 55% to about 65% by weight on a dry matter basis.

In some contemplated embodiments, the composition comprises a fat content of from about 13% to about 20% by weight on a dry matter basis, a protein content of from about 55% to about 65% by weight on a dry matter basis, a carbohydrate content of less than about 11% by weight on a dry matter basis, omega-3 polyunsaturated fatty acids and omega-6 polyunsaturated fatty acids such that the weight ratio of the omega-6 polyunsaturated fatty acids to the omega-3 polyunsaturated fatty acids is from about 0.3:1 to about 5:1, the concentration of omega-3 polyunsaturated fatty acids with less than 20 carbon atoms is from about 0.9% to about 1.2% by weight of the composition on a dry matter basis, the concentration of omega-3 polyunsaturated fatty acids with greater than 20 carbon atoms is from about 4.2% to about 6.0% by weight of the composition on a dry matter basis, the concentration of omega-6 polyunsaturated fatty acids with less than 20 carbon atoms is from about 1.9% to about 4.8% by weight of the composition on a dry matter basis, and the concentration of omega-6 polyunsaturated fatty acids with greater than 20 carbon atoms is from about 1.0% to about 1.3% by weight of the composition on a dry matter basis.

In some contemplated embodiments, the composition comprises a fat content of at least about 8% by weight on a dry matter basis, a protein content of at least about 49% by weight on a dry matter basis, a carbohydrate content of less than about 30% by weight on a dry matter basis, and omega-3 polyunsaturated fatty acids and omega-6 polyunsaturated fatty acids such that the weight ratio of the omega-6 polyunsaturated fatty acids to the omega-3 polyunsaturated fatty acids is from about 0.3:1 to about 5:1. In some such contemplated embodiments, the composition comprises a protein content of from about 50% to about 75% by weight on a dry matter basis.

In some contemplated embodiments, the composition comprises a fat content of less than about 27% by weight on a dry matter basis, a protein content of at least about 35% by weight on a dry matter basis, a carbohydrate content of less than about 30% by weight on a dry matter basis, and omega-3 polyunsaturated fatty acids and omega-6 polyunsaturated fatty acids such that the weight ratio of the omega-6 polyunsaturated fatty acids to the omega-3 polyunsaturated fatty acids is from about 0.3:1 to about 5:1. In some such contemplated embodiments, the composition comprises a fat content of less than about 25% by weight on a dry matter basis.

In some contemplated embodiments, the composition comprises a fat content of less than about 27% by weight on a dry matter basis, a protein content of from about 50% to about 75% by weight on a dry matter basis, a carbohydrate content of from about 6% to about 11% by weight on a dry matter basis, and omega-3 polyunsaturated fatty acids and omega-6 polyunsaturated fatty acids such that the weight ratio of the omega-6 polyunsaturated fatty acids to the omega-3 polyunsaturated fatty acids is from about 0.3:1 to about 5:1.

Specific preferred amounts for each component in a composition will depend on a variety of factors including, for example, the species of animal consuming the composition; the particular components included in the composition; the age, weight, general health, sex, and diet of the animal; the animal's consumption rate; the type of condition(s) being treated; and the like. Thus, the component amounts may vary widely, and may even deviate from the preferred proportions set forth in this patent. Generally, however, the composition (particularly when the composition is a food) will be nutritionally balanced.

The fat and carbohydrate in the compositions of the present invention may be supplied by a variety of sources, including, for example, meat, meat by-products, other animal or plant protein sources, grains, and mixtures thereof. Meat includes, for example, the flesh of poultry; fish; and mammals (e.g., cattle, swine, sheep, goats, and the like). Meat by-products include, for example, lungs, kidneys, brain, livers, and stomachs and intestines freed of their contents. Grains include, for example, wheat, corn, barley, and rice.

The omega-3 and omega-6 polyunsaturated fatty acids may be obtained from a variety of sources. One convenient source is fish oils from, for example, menhaden, mackerel, herring, anchovy, and salmon. The omega-3 polyunsaturated fatty acids, C20:5 eicosapentaenoic acid and C22:6 docosahexaenoic acid, are typical fatty acids present in such fish oils, and, together often make up a significant portion of the oil, such as from about 25% to about 38% of the oil. Omega-6 polyunsaturated fatty acids include, for example, linoleic acid and arachidonic acid. Suitable sources for these fatty acids include, for example, animal fats and vegetable oils (e.g., soy oil, canola oil, and corn oil).

Fiber in the compositions of the present invention may be supplied from a variety of sources, including, for example, vegetable fiber sources such as cellulose, beet pulp, peanut hulls, and soy fiber.

Particularly in instances when the composition is animal food, vitamins and minerals preferably are included in amounts required to avoid deficiency and maintain health. These amounts are readily available in the art. The National Research Council (NRC), for example, provides recommended amounts of such ingredients for farm animals. See, e.g., Nutrient Requirements of Swine (10th Rev. Ed., Nat'l Academy Press, Wash. D.C., 1998), Nutrient Requirements of Poultry (9th Rev. Ed., Nat'l Academy Press, Wash. D.C., 1994), Nutrient Requirements of Horses (Fifth Rev. Ed., Nat'l Academy Press, Wash. D.C., 1989), etc. And the American Feed Control Officials (AAFCO), for example, provides recommended amounts of such ingredients for dogs and cats. See American Feed Control Officials, Incorp., Official publication, pp. 126-140 (2003). Examples of vitamins useful as food additives include vitamin A, B1, B2, B6, B12, C, D, E, K, H (biotin), K, folic acid, inositol, niacin, and pantothenic acid. Examples of minerals and trace elements useful as food additives include calcium, phosphorus, sodium, potassium, magnesium, copper, zinc, chloride, and iron salts.

The compositions of the present invention may further contain other additives known in the art. Preferably, such additives are present in amounts that do not impair the purpose and effect provided by the invention. Examples of contemplated additives include, for example, substances that are functionally beneficial to weight management, substances with a stabilizing effect, processing aids, substances that enhance palatability, coloring substances, and substances that provide nutritional benefits.

Contemplated stabilizing substances include, for example, substances that tend to increase the shelf life of the composition. Potentially suitable examples of such substances include, for example, preservatives, antioxidants, synergists and sequestrants, packaging gases, stabilizers, emulsifiers, thickeners, gelling agents, and humectants. Examples of emulsifiers and/or thickening agents include, for example, gelatin, cellulose ethers, starch, starch esters, starch ethers, and modified starches.

Contemplated additives for coloring, palatability, and nutritional purposes include, for example, colorants (e.g., iron oxide, such as the red, yellow, or brown forms); sodium chloride, potassium citrate, potassium chloride, and other edible salts; taurine; choline; vitamins; minerals; and flavoring. Such additives are known in the art. See, e.g., U.S. Pat. No. 3,202,514. See also, U.S. Pat. No. 4,997,671. Flavorants include, for example, dairy product flavorants (e.g., milk or cheese), meat flavorants (e.g., bacon, liver, beef, poultry, or fish), oleoresin, pinacol, and the various flavorants identified in the trade by a FEMA (Flavor Extract Manufacturers Association) number. Flavorants help provide additional palatability, and are known in the art. See, e.g., U.S. Pat. No. 4,997, 672. See also, U.S. Pat. No. 5,004,624. See also, U.S. Pat. No. 5,114,704. See also, U.S. Pat. No. 5,532,010. See also, U.S. Pat. No. 6,379,727.

The concentration of such additives in the composition typically is up to about 5% by weight on a dry matter basis. In some embodiments, the concentration of such additives (particularly where such additives are primarily nutritional balancing agents, such as vitamins and minerals) is from about 0% to about 2.0% by weight on a dry matter basis. In some embodiments, the concentration of such additives (again, particularly where such additives are primarily nutritional balancing agents) is from about 0% to about 1.0% by weight on a dry matter basis.

A "food" is a nutritionally complete diet for the intended recipient animal (e.g., domestic cat or domestic dog). A "nutritionally complete diet" is a diet that includes sufficient nutrients for maintenance of normal health of a healthy animal on the diet.

"Supplements" include, for example, a feed used with another feed to improve the nutritive balance or performance of the total. Contemplated supplements include compositions that are fed undiluted as a supplement to other feeds, offered free choice with other parts of an animal's ration that are separately available, or diluted and mixed with an animal's regular feed to produce a complete feed. The AAFCO, for example, provides a discussion relating to supplements in the American Feed Control Officials, Incorp. Official Publication, p. 220 (2003). Supplements may be in various forms including, for example, powders, liquids, syrups, pills, etc.

"Treats" include, for example, compositions given to an animal (e.g., a domestic cat or domestic dog) to entice the animal to eat during a non-meal time. Contemplated treats for canines include, for example, dog bones. Treats may be nutritional, wherein the composition comprises one or more nutrients, and may, for example, have a composition as described above for food. Non-nutritional treats encompass any other treats that are non-toxic. A composition of this invention can itself form the treat, be coated onto an existing treat, or both.

Toys include, for example, chewable toys. Contemplated toys for dogs include, for example, artificial bones. A composition of this invention can form a coating on the surface of a toy or on the surface of a component of a toy, be incorporated partially or fully throughout the toy, or both. In a contemplated embodiment, the composition of this invention is orally accessible by the intended user. There a wide range of suitable toys currently marketed. See, e.g., U.S. Pat. No. 5,339,771. See also, e.g., U.S. Pat. No. 5,419,283. It should be recognized that this invention contemplates both partially consumable toys (e.g., toys comprising plastic components) and fully consumable toys (e.g., rawhides and various artificial bones). It should be further recognized that this invention contemplates toys for both human and non-human use, particularly for companion, farm, and zoo animal use, and particularly for dog, cat, or bird use.

The compositions of this invention are not intended to be restricted by any specific listing of proteinaceous, fat, or carbohydrate ingredients or product form. The compositions (particularly foods) can be prepared in, for example, a dry, canned, wet, or intermediate moisture form using conventional pet food processes. In some embodiments, the moisture content is from about 10% to about 90% of the total weight of the composition. In other embodiments, the moisture content is from about 65% to about 75% of the total weight of the composition.

In preparing a composition of the present invention, any ingredient (e.g., fish oil) generally may, for example, be incorporated into the composition during the processing of the formulation, such as during and/or after mixing of other components of the composition. Distribution of these components into the composition can be accomplished by conventional means. In one contemplated embodiment, ground animal and poultry proteinaceous tissues are mixed with the other ingredients, including fish oils, cereal grains, other nutritionally balancing ingredients, special-purpose additives (e.g., vitamin and mineral mixtures, inorganic salts, cellulose and beet pulp, bulking agents, and the like); and water that sufficient for processing is also added. These ingredients preferably are mixed in a vessel suitable for heating while blending the components. Heating of the mixture may be effected using any suitable manner, such as, for example, by direct steam injection or by using a vessel fitted with a heat exchanger. Following the addition of the last ingredient, the mixture is heated to a temperature range of from about 50° F. to about 212° F. In some embodiments, the mixture is heated to a temperature range of from about 70° F. to about 140° F. Temperatures outside these ranges are generally acceptable, but may be commercially impractical without use of other processing aids. When heated to the appropriate temperature, the material will typically be in the form of a thick liquid. The thick liquid is filled into cans. A lid is applied, and the container is hermetically sealed. The sealed can is then placed into conventional equipment designed to sterilize the contents. This is usually accomplished by heating to temperatures of greater than about 230° F. for an appropriate time, which is dependent on, for example, the temperature used and the composition.

Compositions of the present invention (particularly foods) can be prepared in a dry form using conventional processes. In one contemplated embodiment, dry ingredients, including, for example, animal protein sources, plant protein sources, grains, etc., are ground and mixed together. Moist or liquid ingredients, including fats, oils, animal protein sources, water, etc., are then added to and mixed with the dry mix. The mixture is then processed into kibbles or similar dry pieces. Kibble is often formed using an extrusion process in which the mixture of dry and wet ingredients is subjected to mechanical work at a high pressure and temperature, and forced through small openings and cut off into kibble by a rotating knife. The wet kibble is then dried and optionally coated with one or more topical coatings which may include, for example, flavors, fats, oils, powders, and the like. Kibble also can be made from the dough using a baking process, rather than extrusion, wherein the dough is placed into a mold before dry-heat processing.

Treats of the present invention can be prepared by, for example, an extrusion or baking process similar to those described above for dry food. Other processes also may be used to either coat a composition of this invention on the exterior of existing treat forms, or inject it into an existing treat form.

Animal toys of the present invention are typically prepared by coating an existing toy with a composition of this invention.

As noted previously, this invention is directed, in part, to a method for reducing MAP kinase activity in an animal. The method comprises feeding a composition of this invention to the animal. The composition may comprise, for example, the animal's food, a treat, a nutritional supplement, and/or a toy. In a preferred embodiment, the composition comprises the animal's food. In that instance, the composition comprises sufficient (or at least substantially sufficient) nutrients for maintenance of normal health of an identical animal in a healthy condition. In another embodiment, the composition comprises a nutritional supplement. Regardless of the form of the composition, the composition (or a combination of compositions of this invention) is preferably given to the animal in an amount effective to reduce, inhibit, or delay the onset of MAP kinase activity in the animal. MAP kinase activity may be assessed via various techniques known in the art, such as those described below in the Example.

This invention also is directed, in part, to a method for treating cancer, particularly a cancer associated with or dependent on MAP kinase activity, or a cancer treatable by reducing, inhibiting, or delaying the onset of MAP kinase activity. The method comprises feeding a composition of this invention to an animal having the cancer or pre-disposed to having the cancer. The composition may comprise, for example, the animal's food, a treat, a nutritional supplement, and/or a toy. In a preferred embodiment, the composition comprises the animal's food. In that instance, the composition comprises sufficient (or at least substantially sufficient) nutrients for maintenance of normal health of an identical animal in a healthy condition (i.e., an animal that is identical, except not afflicted with the cancer or a pre-disposition to the cancer). In another embodiment, the composition comprises a nutritional supplement. Regardless of the form of the composition, the composition (or a combination of compositions of this invention) is preferably given to the animal in an amount effective to reduce, inhibit, or delay the onset of MAP kinase activity in the animal. As noted above, MAP kinase activity may be assessed via various techniques known in the art.

This invention also is directed, in part, to a method for treating tissue hyperplasias, particularly hyperplasias associated with or dependent on MAP kinase activity, or a hyperplasia treatable by reducing, inhibiting, or delaying the onset of MAP kinase activity. Contemplated hyperplasias include, for example, hyperplasias of the gastrointestinal tract, immune system, prostate, kidney, mammary glands, and heart. The method comprises feeding a composition of this invention to an animal having the cancer or pre-disposed to having the hyperplasia. The composition may comprise, for example, the animal's food, a treat, a nutritional supplement, and/or a toy. In a preferred embodiment, the composition comprises the animal's food. In that instance, the composition comprises sufficient (or at least substantially sufficient) nutrients for maintenance of normal health of an identical animal in a healthy condition (i.e., an animal that is identical, except not afflicted with the hyperplasia or a pre-disposition to the hyperplasia). In another embodiment, the composition comprises a nutritional supplement. Regardless of the form of the composition, the composition (or a combination of compositions of this invention) is preferably given to the animal in an amount effective to reduce, inhibit, or delay the onset of MAP kinase activity in the animal. As noted above, MAP kinase activity may be assessed via various techniques known in the art.

EXAMPLE

The following example is merely illustrative, and not limiting to this disclosure in any way.

We formulated four canned feline diets that were high in protein, low in carbohydrate, and high in fat as described in Table 11 below:

TABLE 11

Ingredient Composition of Pet Food Products

| Component | % by weight on a dry matter basis |
|---|---|
| Meats (liver, lungs, beef muscle, chicken muscle) | 48% to 58% |
| Cereal proteins & egg proteins | 4% to 9% |
| Water | 24% to 27% |
| Fish oil (a source of N-3 fatty acids) | 0.5% to 5.7% |
| Soybean oil (a source of N-6 fatty acids) | 2% to 2.5% |
| Minerals | 0.7% |
| Vitamins | 0.32% to 1.22% |
| Gum | 0.35% to 0.5% |
| Natural flavorings | 1.0% |

About 10% of the total fat in each diet was polyunsaturated fatty acids. The ratio of omega-6 to omega-3 fatty acids ranged from 0.4:1 to about 5:1. Specifically, the diets had the following ratios: Diet 1: from about 4.5 to about 5; Diet 2: from about 2.3 to about 2.5; Diet 3: from about 1 to about 1.2; and Diet 4: from about 0.4 to about 0.5. The diets were each fed to a separate group of healthy cats for 24 weeks. Blood and adipose tissue were collected at baseline and after 6, 12, and 24 weeks.

FIG. 1 shows the observed change in polyunsaturated fatty acid from baseline in adipose tissue as a function of the ratio of omega-6 to omega-3 fatty acid in the diet.

Figure 2:
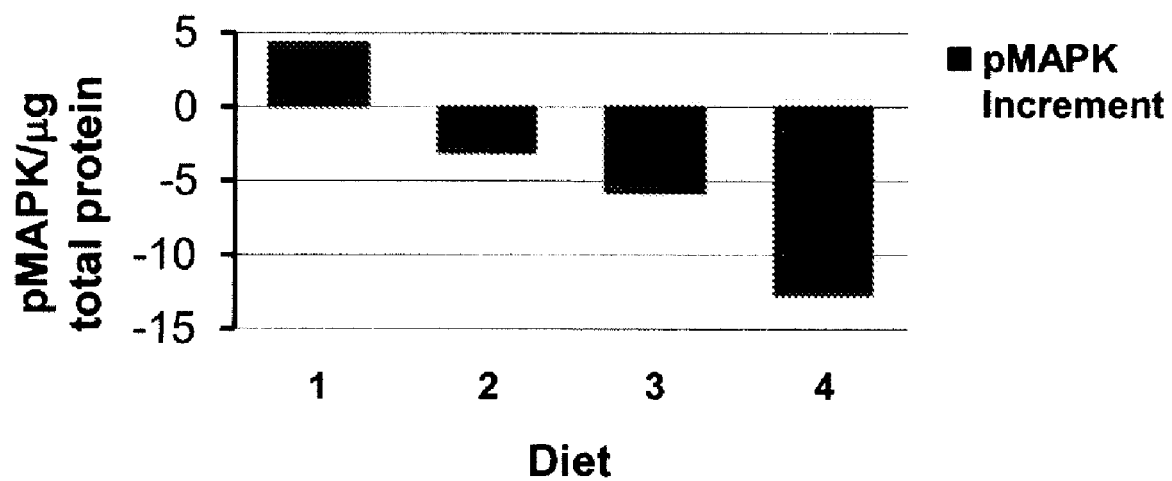
FIG. 2 illustrates the observed incremental effects on mitogen-activated protein kinase (MAPK) activity in adipose tissue as a function of the ratio of omega-6 to omega-3 fatty acid in the diet. In this experiment, the tested diets had the following n6:n3 ratios: Diet 1: from about 4.5 to about 5; Diet 2: from about 2.3 to about 2.5; Diet 3: from about 1 to about 1.2; and Diet 4: from about 0.4 to about 0.5.

FIG. 2 shows the observed incremental effects on mitogen-activated protein kinase activity in adipose tissue as a function of the ratio of omega-6 to omega-3 fatty acid in the diet. As can be seen, 2, 3, and 4 reduced the activity of mitogen-activated protein kinase in adipose tissue.

Figure 3:
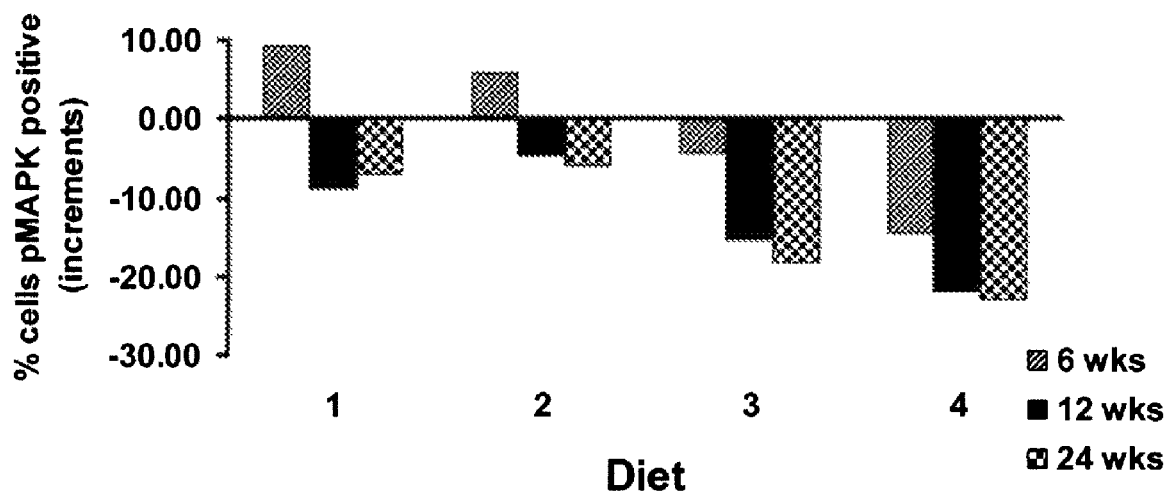
FIG. 3 illustrates the observed change in mitogen-activated protein kinase activity from baseline in white blood cells as a function of the ratio of omega-6 to omega-3 fatty acid in the diet. In this experiment, the tested diets had the following n6:n3 ratios: Diet 1: from about 4.5 to about 5; Diet 2: from about 2.3 to about 2.5; Diet 3: from about 1 to about 1.2; and Diet 4: from about 0.4 to about 0.5.

FIG. 3 shows the observed change in mitogen-activated protein kinase activity from baseline in white blood cells as a function of the ratio of omega-6 to omega-3 fatty acid in the diet. As can be seen, all four diets reduced the activity of mitogen-activated protein kinase in white blood cells.

All the references cited above are incorporated by reference into this patent.

The words "comprise", "comprises", and "comprising" are to be interpreted inclusively rather than exclusively.

Except to the extent stated otherwise, all percentages used in this specification are weight percentages on a dry matter basis. The phrase "dry matter basis" means the component concentration in the composition after any moisture in the composition is removed.

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

We claim:

1. A method for reducing mitogen-activated-protein kinase activity in an animal, wherein the method comprises feeding the animal a composition comprising:
   a fat content of from about 13% to about 20% by weight on a dry matter basis,
   a protein content of from about 55% to about 65% by weight on a dry matter basis, and
   a carbohydrate content of less than 11% by weight on a dry matter basis;
   wherein the weight ratio of the omega-6 polyunsaturated fatty acids to the omega-3 polyunsaturated fatty acids is from about 0.3:1 to about 5:1;
   wherein the omega-3 polyunsaturated fatty acids comprise fatty acids with less than 20 carbon atoms, and fatty acids with greater than 20 carbon atoms; and
   the omega-6 polyunsaturated fatty, acids comprise fatty acids with less than 20 carbon atoms, and fatty acids with greater than 20 carbon atoms; and
   the concentration of omega-3 polyunsaturated fatty acids with less than 20 carbon atoms is from about 0.9% to about 1.2% by weight of the composition on a dry matter basis; and
   the concentration of omega-3 polyunsaturated fatty acids with greater than 20 carbon atoms is from about 4.2% to about 6.0% by weight of the composition on a dry matter basis; and
   the concentration of omega-6 polyunsaturated fatty acids with less than 20 carbon atoms is from about 1.9% to about 4.8% by weight of the composition on a dry matter basis; and
   the concentration of omega-6 polyunsaturated fatty acids with greater than 20 carbon atoms is from about 1.0% to about 1.3% by weight of the composition on a dry matter basis; and
   wherein mitogen-activated-protein kinase activity is reduced in the animal.

2. A method for treating a cancer or tissue hyperplasia in an animal, wherein the method comprises feeding the animal a composition comprising: a fat content of from about 13% to about 20% by weight on a dry matter basis, a protein content of from about 55% to about 65% by weight on a dry matter basis, and a carbohydrate content of less than 11% by weight on a dry matter basis;
   wherein the weight ratio of the omega-6 polyunsaturated fatty acids to the omega-3 polyunsaturated fatty acids is from about 0.3:1 to about 5:1;
   wherein the omega-3 polyunsaturated fatty acids comprise fatty acids with less than 20 carbon atoms, and fatty acids with greater than 20 carbon atoms; and
   the omega-6 polyunsaturated fatty acids comprise fatty acids with less than 20 carbon atoms, and fatty acids with greater than 20 carbon atoms; and
   the concentration of omega-3 polyunsaturated fatty acids with less than 20 carbon atoms is from about 0.9% to about 1.2% by weight of the composition on a dry matter basis; and
   the concentration of omega-3 polyunsaturated fatty acids with greater than 20 carbon atoms is from about 4.2% to about 6.0% by weight of the composition on a dry matter basis; and
   the concentration of omega-6 polyunsaturated fatty acids with less than 20 carbon atoms is from about 1.9% to about 4.8% by weight of the composition on a dry matter basis; and the concentration of omega-6 polyunsaturated fatty acids with greater than 20 carbon atoms is from about 1.0% to about 1.3% by weight of the composition on a dry matter basis; and
   wherein cancer or tissue hyperplasia is treated in the animal.

3. A method according to claim 2, wherein the animal is a cat or dog.

4. The method of claim 1, wherein the weight ratio of the omega-6 polyunsaturated fatty acids to the omega-3 polyunsaturated fatty acids is one of about 0.4:1 to about 0.5:1, about 1:1 to about 1.2:1, or about 2.3:1 to about 2.5:1.

5. The method of claim 1, wherein the weight ratio of the omega-6 polyunsaturated fatty acids to the omega-3 polyunsaturated fatty acids is 0.4:1 to 0.5:1.

6. The method of claim 2, wherein the weight ratio of the omega-6 polyunsaturated fatty acids to the omega-3 polyunsaturated fatty acids is 0.4:1 to 0.5:1.

* * * * *

UNITED STATES PATENT AND TRADEMARK OFFICE
CERTIFICATE OF CORRECTION

PATENT NO. : 8,399,411 B2
APPLICATION NO. : 12/781360
DATED : March 19, 2013
INVENTOR(S) : Kathy L. Gross et al.

It is certified that error appears in the above-identified patent and that said Letters Patent is hereby corrected as shown below:

In the Claims delete "and" at col. 15, line 48;

add "and omega-3 polyunsaturated fatty acids and omega-6 polyunsaturated fatty acids," after col. 15, line 50;

delete "and" at col. 16, line 21;

add "and omega-3 polyunsaturated fatty acids and omega-6 polyunsaturated fatty acids;" after col. 16, line 22;

Signed and Sealed this
Twenty-sixth Day of November, 2013

Margaret A. Focarino
*Commissioner for Patents of the United States Patent and Trademark Office*